(12) United States Patent
Rossignol

(10) Patent No.: US 7,550,493 B2
(45) Date of Patent: Jun. 23, 2009

(54) HALOGENATED BENZAMIDE DERIVATIVES

(75) Inventor: Jean Francois Rossignol, St. Petersburg, FL (US)

(73) Assignee: Romark Laboratories, LC, Tampa, FL (US)

( * ) Notice: Subject to any disclaimer, the term of this patent is extended or adjusted under 35 U.S.C. 154(b) by 43 days.

(21) Appl. No.: 11/865,541

(22) Filed: Oct. 1, 2007

(65) Prior Publication Data

US 2008/0097106 A1 Apr. 24, 2008

Related U.S. Application Data

(63) Continuation of application No. 11/221,256, filed on Sep. 6, 2005, now Pat. No. 7,285,567.

(60) Provisional application No. 60/608,354, filed on Sep. 9, 2004.

(51) Int. Cl.
*A61K 31/426* (2006.01)
*C07D 277/20* (2006.01)

(52) U.S. Cl. .................. 514/371; 548/146; 548/190; 548/193; 548/194; 548/195; 514/365; 514/370

(58) Field of Classification Search ................. 548/146, 548/190, 193, 195; 514/365, 370, 371
See application file for complete search history.

(56) References Cited

U.S. PATENT DOCUMENTS

| | | | |
|---|---|---|---|
| 3,736,330 A | 5/1973 | Haken et al. | |
| 3,950,351 A | 4/1976 | Rossignol et al. | |
| 5,387,598 A | 2/1995 | Rossignol | |
| 5,578,621 A | 11/1996 | Rossignol | |
| 5,856,348 A | 1/1999 | Rossignol | |
| 5,859,038 A | 1/1999 | Rossignol | |
| 5,886,013 A | 3/1999 | Rossignol | |
| 5,935,591 A | 8/1999 | Rossignol | |
| 5,965,590 A | 10/1999 | Rossignol | |
| 5,968,961 A | 10/1999 | Rossignol | |
| 6,020,353 A | 2/2000 | Rossignol | |
| 6,117,894 A | 9/2000 | Rossignol | |
| 6,737,382 B1 * | 5/2004 | Iwataki et al. | ............... 504/252 |
| 7,037,929 B1 | 5/2006 | Pevarello et al. | |
| 7,285,567 B2 * | 10/2007 | Rossignol | ................... 514/371 |
| 2004/0259877 A1 | 12/2004 | Muto et al. | |

FOREIGN PATENT DOCUMENTS

GB 1 276 663 6/1972

OTHER PUBLICATIONS

Esposito et al. "In Vitro Efficacies of Nitazoxanide and Other Thiazolides against *Neospora caninum* Tachyzoltes Reveal Antiparasitic Activity Independent of the Nitro Group," 2005, Antimicrobial Agents and Chemotherapy, 49(9):3715-3723.
Husain et al. "Search for Patent Anthemintics—Part XIII 2-(3,5-Substituted Salicylamido/Cinnamido)-4,5-Substituted Thiazoles," 1979, Journal of Indian Chemical Society, vol. LVI, pp. 917-918.
Pevarello et al., 2000-STN International HCAPLUS Database, Columbus, Ohio Accession No. 2000:314687.
Amemiya et al., 2001-STN International HCAPLUS Database, Columbus, Ohio Accession No. 2001:816614.
Korba, Brent E., et al. Nitazoxanide, tizoxanide and other thiazolides are potent inhibitors of hepatitis B virus and hepatitis C virus replication; Science Direct, Antiviral Research 77, Aug. 10, 2007; pp. 56-63.

* cited by examiner

*Primary Examiner*—Golam M Shameem
(74) *Attorney, Agent, or Firm*—Novak Druce & Quigg

(57) ABSTRACT

A halogenated benzamide derivative characterized by greater specificity for viral pathogens and less disruptive to beneficial gut microflora, according to formula (III): in which $R_1$ is a halogen atom, and $R_2$-$R_6$ are independently hydrogen, hydroxyl, $C_1$-$C_4$ alkyl, —$C_1$-$C_4$ alkoxy, acyloxy, nitro, halogen, —C(O)$R_7$ where $R_7$ is —$C_1$-$C_4$ alkyl, or, aromatic including salts and hydrates of these compounds and where at least two of $R_2$-$R_6$ are not hydrogen and where at least one of $R_2$-$R_6$ are hydroxy or acyloxy.

8 Claims, No Drawings

HALOGENATED BENZAMIDE DERIVATIVES

CROSS-REFERENCE TO RELATED APPLICATIONS

This application is a continuation of application Ser. No. 11/221,256 filed Sep. 6, 2005, which claims benefit to U.S. Provisional Application Ser. No. 60/608,354 filed Sep. 9, 2004. The entire content of each above-mentioned application is hereby incorporated by reference in entirety.

FIELD OF THE INVENTION

The invention relates to halogenated benzamide derivatives, and more specifically, benzamide derivatives characterized by greater specificity for viral pathogens and less disruptive to beneficial gut microflora.

BACKGROUND OF THE INVENTION

Laser (2-(acetolyloxy)-N-(5-nitro-2-thiazolyl)benzamide, the compound of formula (I), also referred to as nitrothiazole, nitazoxanide, or NTZ, is known for use in the treatment and prevention of parasitic infections, bacterial infections, fungal infections, diarrhea and other intestinal troubles (U.S. Pat. Nos. 3,950,351, 4,315,018 and 5,578,621) including treatment of trematodes (U.S. Pat. No. 5,856,348). The preparation of NTZ is disclosed in U.S. Pat. No. 3,950,351. Improved pharmaceutical compositions for delivery of NTZ are disclosed U.S. Pat. Nos. 6,117,894 and 5,968,961.

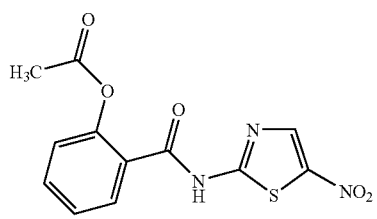

(I)

It has been postulated that, in anaerobic bacteria and protozoa, NTZ exhibits a mode of action based upon reduction of its nitro group by nitroreductases, and particularly pyruvate ferredoxin oxidoreductase (PFOR) dependent electron transfer reactions that are essential for anaerobic energy metabolism. Nothing is currently known regarding the possible mode of action of NTZ for helminthes, however, the enzymes of anaerobic electron transport are considered as potential targets, with the 5-nitro group implicated in this mechanism.

Compounds according to formula (II), in which one of $R_{1-5}$ is —OH and the remainder of $R_{1-5}$ being H, are known to exhibit antiviral activity, and are known for treatment of human viral diseases such as those caused by human cytomegalovirus, varicella zoster, Epstein Barr virus, HSV-I and HSV-II (U.S. Pat. Nos. 5,886,013 and 6,020,353).

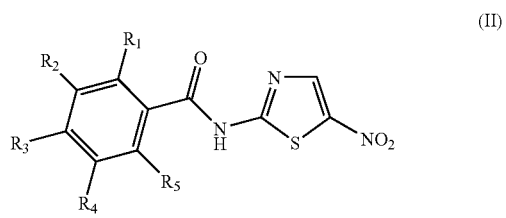

(II)

While potent, these compounds are not selective for only viral pathogens. They are described as having excellent efficacy against parasites, bacteria and fungus. In practice, this is associated with a problem. Namely, in humans and many animals, the gut contains beneficial populations of microflora, principally comprised of anaerobic bacteria. Oral administration of broad spectrum compounds such as those of Formula (II) kills the bacterial gut flora, which may lead to secondary complications including diarrhea requiring further treatment.

Accordingly, there is a need for therapeutic compounds that are more selective for viral pathogens. Most preferably, these compounds should possess antiviral activity, but be substantially devoid of antibacterial and antiparasite activity, at least to the extent of avoiding deleterious effects upon the beneficial gut microflora when administered orally.

This need, and more, is achieved by the present invention, as will become clear to one of ordinary skill upon reading the following disclosure and examples.

SUMMARY OF THE INVENTION

The present invention relates to antiviral benzamide derivatives that are more selective for viral pathogens, and accordingly cause reduced deleterious effects upon beneficial gut microflora when administered orally.

In a first aspect, the invention is surprisingly made by replacing the nitro substituent, which has until now been believed to be the key to the activity of NTZ, with a halogen atom. This substitution may be made in any of the known therapeutically effective 2-benzamido-5-nitro-thizaoles (wherein the benzene ring may be variously substituted). Surprisingly, the novel halogenated compounds retain their antiviral properties, but they lack activity against the bacterial gut microflora when administered orally.

Examples of these known 2-benzamido-5-nitro-thizaoles, which are analogues of the compounds of the present invention differing only in that in accordance with the present invention the nitro group is removed and replaced with a halogen atom, are extensively set forth in the above referenced U.S. Patents, and U.S. Pat. No. 5,886,013 in particular, their disclosure being incorporated herein by reference.

The present invention further provides (5-halo-2-thiazolyl) benzamide compounds according to formula (III):

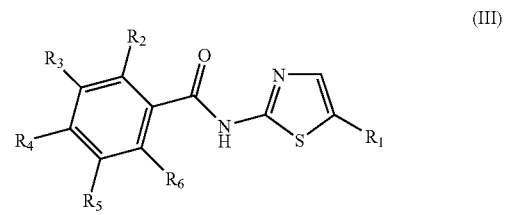

(III)

in which $R_1$ is a halogen atom, preferably F, Cl, Br, or I, more preferably Br or Cl, most preferably Br, and $R_2$-$R_6$ are independently hydrogen, hydroxyl, $C_1$-$C_4$ alkyl, —$C_1$-$C_4$ alkoxy, acyloxy (preferably acetoxy or propionoxy), nitro, halogen, —C(O)$R_7$ where $R_7$ is —$C_1$-$C_4$ alkyl, or, aromatic (preferably unsubstituted or substituted phenyl or benzyl), including salts and hydrates of these compounds.

Preferably, one of $R_2$-$R_6$ is hydroxyl.

Preferably at least one of $R_2$-$R_6$ are other than hydrogen, and more preferably at least two of $R_2$-$R_6$ are other than hydrogen.

Two adjacent $R_2$-$R_6$ may together form a benzyl ring.

Preferably, $R_2$-$R_6$ include no more than one acyloxy and no more than one halogen.

The present invention further provides antiviral compounds according to formula (IV):

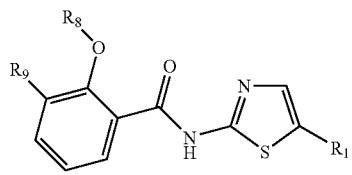
(IV)

in which $R_1$ is a halogen atom, $R_8$ is —C(O)$R_{10}$, where $R_{10}$ is —$C_1$-$C_4$ alkyl, and $R_9$ is —$C_1$-$C_4$ alkyl or —$C_1$-$C_4$ alkoxy, including salts and hydrates of these compounds.

The invention further provides antiviral pharmaceutical compositions comprising a compound of Formula (III) or (IV) and a pharmaceutically acceptable carrier.

Finally, the invention provides a method of treating or preventing a viral infection in an animal or human subject, the method comprising administering to said subject at least one dose of the pharmaceutical composition comprising an effective amount of the antiviral compound according to Formula (III) or (IV) and a pharmaceutically acceptable carrier.

DETAILED DESCRIPTION

In Compounds of the present invention include those according to formula (III):

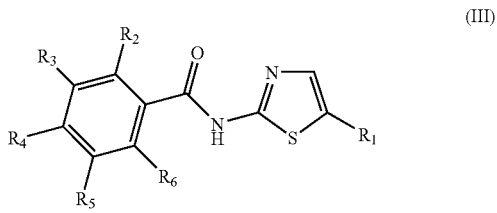
(III)

in which $R_1$ is a halogen atom, preferably F, Cl, Br, or I, more preferably Br or Cl, most preferably Br, and $R_2$-$R_6$ are independently hydrogen, hydroxyl, $C_1$-$C_4$ alkyl, —$C_1$-$C_4$ alkoxy, acyloxy (preferably acetoxy or propionoxy), nitro, halogen, —C(O)$R_7$ where $R_7$ is —$C_1$-$C_4$ alkyl, or, aromatic (preferably phenyl or benzyl, which may be further substituted), including salts and hydrates of these compounds.

Preferably, one of $R_2$-$R_6$ is hydroxyl.

Preferably at least one of $R_2$-$R_6$ are other than hydrogen, and more preferably at least two of $R_2$-$R_6$ are other than hydrogen.

Two adjacent $R_2$-$R_6$ may together form a benzyl ring.

Preferably, $R_2$-$R_6$ include no more than one acyloxy and no more than one halogen. Compounds according to the present invention are illustrated by the following non-limiting list:

| Code Number | Structure | Molecular Weight | Molecular Formula |
|---|---|---|---|
| RM-4803 | 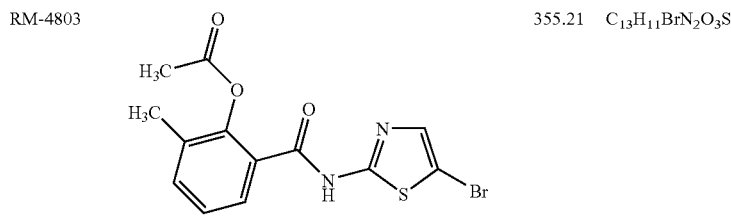 | 355.21 | $C_{13}H_{11}BrN_2O_3S$ |
| RM-4804 | 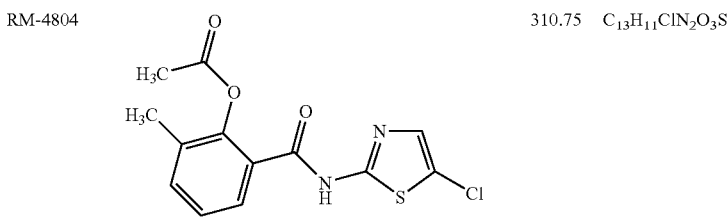 | 310.75 | $C_{13}H_{11}ClN_2O_3S$ |

-continued

| Code Number | Structure | Molecular Weight | Molecular Formula |
|---|---|---|---|
| RM-4806 | 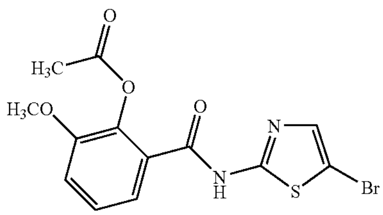 | 371.21 | $C_{13}H_{11}BrN_2O_4S$ |
| RM-4819 | 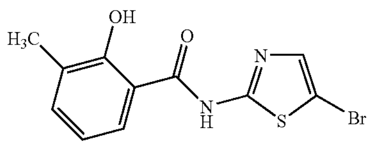 | 313.17 | $C_{11}H_9BrN_2O_2S$ |
| RM-4820 | 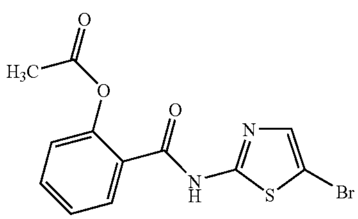 | 341.18 | $C_{12}H_9BrN_2O_3S$ |
| RM-4821 | 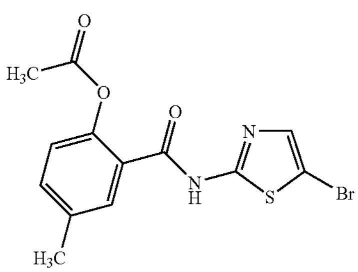 | 355.21 | $C_{13}H_{11}BrN_2O_3S$ |
| RM-4822 | 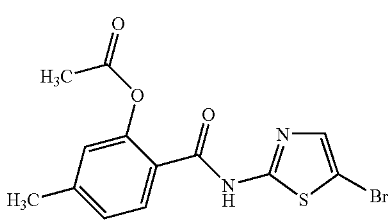 | 355.21 | $C_{13}H_{11}BrN_2O_3S$ |
| RM-4826 | 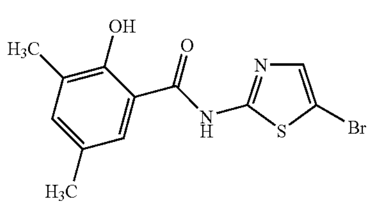 | 313.17 | $C_{11}H_9BrN_2O_2S$ |
| RM-4827 | 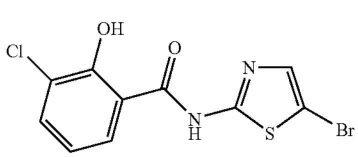 | 333.59 | $C_{10}H_6BrClN_2O_2S$ |

-continued
| Code Number | Structure | Molecular Weight | Molecular Formula |
|---|---|---|---|
| RM-4831 | 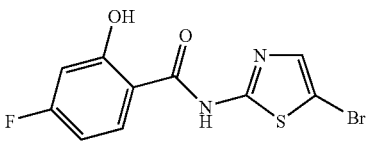 | 317.13 | $C_{10}H_6BrFN_2O_2S$ |
| RM-4832 | 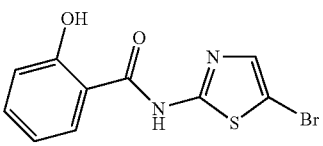 | 299.14 | $C_{10}H_7BrN_2O_2S$ |
| RM-4833 | 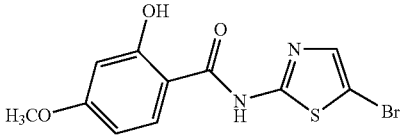 | 329.17 | $C_{11}H_9BrN_2O_3S$ |
| RM-4834 | 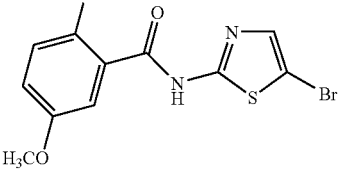 | 329.17 | $C_{11}H_9BrN_2O_3S$ |
| RM-4835 | 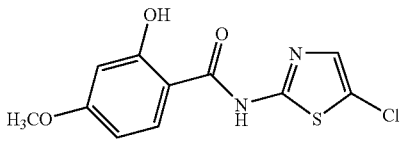 | 284.72 | $C_{11}H_9ClN_2O_3S$ |
| RM-4836 | 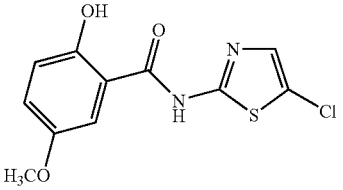 | 284.72 | $C_{11}H_9ClN_2O_3S$ |
| RM-4838 | 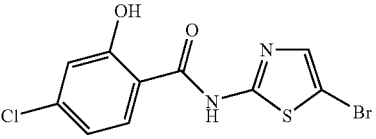 | 333.59 | $C_{10}H_6BrClN_2O_2S$ |
| RM-4839 | 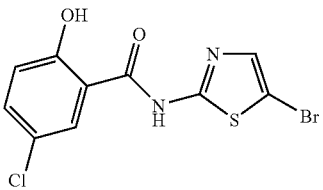 | 333.59 | $C_{10}H_6BrClN_2O_2S$ |

-continued

| Code Number | Structure | Molecular Weight | Molecular Formula |
|---|---|---|---|
| RM-4840 | 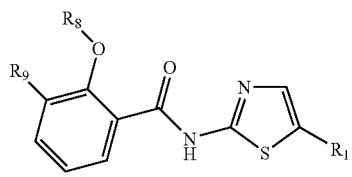 | 378.04 | $C_{10}H_6Br_2N_2O_2S$ |

Preferred examples of compounds within Formula (III) include:
2-(acetolyloxy)-3-methyl-N-(5-bromo-2-thiazolyl)benzamide (RM4803);
2-(hydroxy)-3-methyl-N-(5-bromo-2-thiazolyl)benzamide (RM4819);
2-(acetolyloxy)-N-(5-bromo-2-thiazolyl)benzamide (RM4820);
2-(acetolyloxy)-5-methoxy-N-(5-bromo-2-thiazolyl)benzamide (RM4821); and
2-(acetolyloxy)-5-methoxy-N-(5-bromo-2-thiazolyl)benzamide (RM4822).

It has further been discovered that compounds with a hydroxyl substitutent in the ortho position of the benzene ring have good efficacy. Thus, from among the above illustrative compounds, the following compounds are preferred: RM-4819, RM-4826, RM-4827, RM-4831, RM-4832, RM-4833, RM-4834, RM-4835, RM-4836, RM-4838, RM-4839, RM-4840.

Compounds according to the invention preferably include those of formula (IV):

(IV)

wherein:
$R_1$ is halogen, preferably F, Cl, Br, or I, more preferably Br or Cl, most preferably Br,
$R_8$ is —C(O)$R_{10}$, in which $R_{10}$ is —$C_1$-$C_4$ arkyl. $R_{10}$ includes methyl, ethyl, propyl and butyl, including isomers thereof. Methyl is preferred, whereby the benzamide substituent is acetolyloxy, and
$R_9$ is —$C_1$-$C_4$ alkyl or —$C_1$-$C_4$ alkoxy. Methyl and methoxy are preferred. Methyl is most preferred.

Examples of compounds within Formula (IV) include:
2-(acetolyloxy)-3-methyl-N-(5-bromo-2-thiazolyl)benzamide (RM4803);
2-(acetolyloxy)-3-methyl-N-(5-chloro-2-thiazolyl)benzamide (RM4804); and
2-(acetolyloxy)-3-methoxy-N-(5-bromo-2-thiazolyl)benzamide (RM4806).

The compositions of the present invention may be formulated as solid or liquid dosage forms, or as pastes or ointments, and may optionally contain further active ingredients.

The pharmaceutical compositions of the present invention comprise a pharmaceutically acceptable carrier, which is not particularly limited, and includes a wide range of carriers known to those of ordinary skill in the art, and including wetting or dispersing agents (U.S. Pat. No. 5,578,621), starch derivatives (U.S. Pat. No. 5,578,621), excipients, and the like. Tablet embodiments may optionally comprise a coating of a substance that constitutes an enteric coating, i.e. a coating that substantially insoluble in gastric secretion but substantially soluble in intestinal fluids.

Pharmaceutical compositions comprising compounds according to Formula (III) or (IV) are preferably formulated for oral administration and are optionally in the form of a liquid, for example an emulsion or a solution or a suspension in water or oil such as arachis oil, or other liquid. Formulations of non-aqueous micellar solutions may be prepared according to the method disclosed in U.S. Pat. No. 5,169,846. Alternatively, tablets can be manufactured, for example, by performing the following steps: wet granulation; drying; and compression. Film coating is generally performed with organic solvents.

The term "selective antiviral" as used herein means that, at dosages effective for the prevention or treatment of a viral disease, the activity is more antiviral than antibacterial, antifangal, or antiparasite, and gut flora of the subject is not disrupted to levels expected with broad spectrum antibiotics.

The preferred antiviral treatment or prophylactic dosages of the compounds of the present invention may depend upon the weight of the subject, and may be inferred by one of ordinary skill without undue experimentation by reference to the following examples, which are set forth for purposes of illustration and are not intended to be limiting.

EXAMPLE 1

Testing Against Viruses

Methods

Non-Hepatic Viruses

Cell cultures and Treatments. HEp-2 laryngeal carcinoma cells, monkey kidney 37RC, MA104 and VERO cells, canine Madin-Darby kidney (MDCK) and mammary adenocarcinoma (A72) cells, were grown at 37° C. in a 5% $CO_2$ atmosphere in RPMI medium (Gibco-Invitrogen, Carlsbad, Calif.), supplemented with 10% fetal calf serum (FCS), 2 mM glutamine and antibiotics. Compounds dissolved in DMSO stock solution (50 mg/ml) were diluted in culture medium and added to infected cells immediately after the 1 hour adsorption period. Compounds were maintained in the medium for the duration of the experiment. Controls received equal amounts of DMSO diluent. Each concentration of each compound was tested in duplicate and each experiment was repeated twice.

Virus infection and titration. The following viruses were utilized: Influenza A: strain Puertorico (PR8); Paramyxovirus (Parainfluenza): Sendai virus (SV); Rhabdovirus: Vesicular Stomatitis Virus (VSV); Rotavirus: Simian Rotavirus SA-11 (SA-11); Herpes Simplex virus type 1: strain F1 (HSV-1); Coronavirus: canine coronavirus strain S-378 (CCoV). Confluent cell monolayers were infected with Influenza A virus (MDCK cells) or parainfluenza SV (37RC cells) for 1 h at 37° C. at a multiplicity of infection (m.o.i.) of 5 HAU (Hemagglutinating Units)/$10.\sup.5$ cells. Alternatively, confluent cell monolayers were infected with HSV-1 (HEp-2 cells), VSV (MA104 cells), CCoV (A72 cells) or Rotavirus SA-11 (MA104 cells) for 1 h at 37° C. at a m.o.i. of 5 PFU (Plaque Forming Units)/$10^5$ cells for HSV-1, VSV and CCoV and 1 PFU/$10^5$ cells for SA-11. After the adsorption period, the viral inoculum was removed and cell monolayers were washed three times with phosphate-buffer saline (PBS). Cells were maintained at 37° C. in appropriate culture medium containing 2% FCS in the presence of the test compound or control diluent. Virus yield was determined 24 hours post infection (p.i.) by hemagglutinin titration (WSN, PR8, SV and SA-11) or CPE50% assay (VSV, HSV-1, and CCoV), according to standard procedures (Amici, C., Belardo, G., Rossi, A. & Santoro, M. G. *Activation of IκB kinase by Herpes Simplex virus type 1. A novel target for anti-herpetic therapy. J. Biol. Chem.* 276, 28759-28766 (2001) and Bemasconi, D., Amici, C., La Frazia, S., Ianaro, A. & Santoro, M. G. *The IκB kinase is a key factor in triggering Influenza A virus—induced inflammatory cytochine production in airway epithelial cells. J. Biol. Chem.* 280, 24127-24134 (2005)).

Cell toxicity. Cell viability was determined by the 3-(4,5-dimethylthiazol-2-yl)-2,5-diphenyltetrazolium bromide (MTT) to MTT formazan conversion assay (Sigma-Aldrich, St Louis, Mo.). For MTT assay, reduced MTT (formazan) was extracted from cells by adding 100.mu.l of acidic isopropanol containing 10% Triton X-100, and formazan absorbance was measured in an ELISA microplate reader at two different wavelengths (540 and 690 nm).

Hepatitis B Virus

Anti-Hepatitis B Virus (HBV) analyses and an assessment of cytotoxicity were performed in a 9-day assay in the chronically-producing HBV human hepatoblastoma cell line, 2.2.15, as previously described (Korba, B. E. & Gerin, J. L. *Use of a standardized cell culture assay to assess activities of nucleosides analogues against hepatitis B virus replication. Antivir. Res.* 19, 55-70 (1992)).

replicon-containing human hepatoblastoma cell line, AVA5 (Okuse, C., Rinaudo, J. A., Farrar, K., Wells, F. & Korba, B. E. *Enhancement of antiviral activity against hepatitis C virus in vitro by interferon combination therapy. Antivir. Res.* 65, 23-34 (2005)) as previously described (Blight, K. J., Kolykhalov, A. A. & Rice, C. M. *Efficient initiation of HCV RNA replication in cell culture. Science* 290, 1972-1974 (2000)).

Results of Testing Against Viruses

TABLE 2

Activity of other compounds against paramyxovirus: sendai virus in cell culture.

| | Paramyxovirus: Sendai virus | |
|---|---|---|
| Compound | $EC_{50}$ (μM) | SI |
| RM-4820 | 0.34 | 35 |
| RM-4821 | 0.36 | >50 |
| RM-4822 | 0.36 | 7 |

$EC_{50}$ = drug concentration at which a 2-fold depression of viral RNA (relative to the average levels in untreated cultures) was observed. $CC_{50}$ = drug concentration at which a 2-fold depression of reduced MTT was observed relative to average levels in untreated cultures. SI (selectivity index) = $CC_{50}/EC_{50}$.

TABLE 1

Activity of RM-4803 and RM-4819 against viruses in cell culture.

| | $EC_{50}$ (μM)/SI | | |
|---|---|---|---|
| Virus | RM4819 | RM4803 | Cell Culture |
| Rotavirus: Simian rotavirus SA-11 | 0.3/>500 | 0.06/>2500 | MA104 |
| Influenza A: PR8 strain | 9.6/>17 | 2.8/>50 | MDCK |
| Paramyxovirus: Sendai virus | 1.3/>125 | 1.1/>125 | 37RC |
| Coronavirus: canine coronavirus strain S-378 | 4.9/>33 | 4.2/13 | A72 |
| Rhabdovirus: Vesicular stomatitis virus | 1.6/>100 | 2.8/>50 | MA104 |
| Herpes Simplex type 1: strain F1 | 0.6/>250 | 5.6/3 | HEp-2 |

$EC_{50}$ = drug concentration at which a 2-fold depression of viral DNA or RNA (relative to the average levels in untreated cultures) was observed. $CC_{50}$ = drug concentration at which a 2-fold depression of reduced MTT was observed relative to average levels in untreated cultures. SI (selectivity index) = $CC_{50}/EC_{50}$.

TABLE 3

Activity of compounds against HBV replication in 2.2.15 cell culture.

| | Extracellular Virion DNA | | Intracellular HBV R.I. | | | Selectivity Index | |
|---|---|---|---|---|---|---|---|
| Compound | $EC_{50}$(μM) | $EC_{90}$(μM) | $EC_{50}$(μM) | $EC_{90}$(μM) | $CC_{50}$(μM) | Virion | R.I. |
| Lamivudine | 0.058 ± 0.006 | 0.164 ± 0.015 | 0.172 ± 0.020 | 0.660 ± 0.068 | 2229 ± 76 | 12959 | 3377 |
| RM4803 | 6.3 ± 0.7 | 15 ± 1.1 | 12 ± 1.5 | 50 ± 5.5 | >1000[§] | >67 | >20 |
| RM4819 | 3.5 ± 0.5 | 9.0 ± 0.8 | 7.6 ± 0.9 | 22 ± 2.6 | >1000[§] | >111 | >46 |

[§]No significant cytotoxic effects were observed up to the highest indicated concentration.

Hepatitis C Virus

Anti-Hepatitis C Virus (HCV) analyses and an assessment of cytotoxicity were performed in a 3-day assay in the HCV Values presented (±standard deviations [S.D.]) were calculated by linear regression analysis using data combined from all treated cultures. S.D. were calculated using the standard error of regression generated from linear regression analyses (QuattroPro.™). $EC_{50}$, $EC_{90}$32 drug concentration at which a 2-fold, or a 10-fold depression of HBV DNA (relative to the average levels in untreated cultures), respectively, was observed, $CC_{50}$=drug concentration at which a 2-fold depression of neutral red dye uptake (relative to the average levels in untreated cultures) was observed, The $EC_{90}$ values were used for the calculation of the Selectivity Indexes [S.I.] since at least a 3-fold depression of HBV levels is typically required to achieve statistical significance in this assay system. HBV R.I.=intracellular HBV DNA replication intermediate.

TABLE 4

Activity of compounds against hepatitis C virus replication in AVA5 cell culture.

| Compound | $CC_{50}$ (μM) | $EC_{50}$ (μM) | $EC_{90}$ (μM) | Selectivity Index |
|---|---|---|---|---|
| ∝-Interferon | >10,000*§ | 2.2 ± 0.2* | 8. ± 0.6* | >4,545 |
| Ribavirin | 61 ± 2.9 | 94 ± 10 | >100§ | 0.6 |
| RM4803 | 282 ± 21 | 37 ± 2.7 | 98 ± 9.3 | 7.6 |
| RM4819 | 164 ± 18 | 8.9 ± 0.7 | 79 ± 8.2 | 18 |

*Values for interferon are expressed as "IU/ml."
§No significant cytotoxic or antiviral effects were observed up to the highest indicated concentration.

Values presented (±standard deviations [S.D.]) were calculated by linear regression analysis using data combined from all treated cultures. S.D. were calculated using the standard error of regression generated from the linear regression analyses (QuattroPro.™). $EC_{50}$, $EC_{90}$=drug concentration at which a 2-fold, or a 10-fold depression of HCV RNA (relative to the average levels in untreated cultures), respectively, was observed. $CC_{50}$=drug concentration at which a 2-fold depression of neutral red dye uptake was observed relative to the average levels in untreated cultures. Selectivity index=$CC_{50}$/$EC_{50}$.

EXAMPLE 2

Testing Against Anaerobic Bacteria

Methods. Recent clinical anaerobic isolates (2000 to date) comprised 40 *B. fragilis* group, 26 *Prevotella/Porphyromonas*, 28 fusobacteria, 16 anaerobic Gram positive cocci, 14 anaerobic Gram-positive non-sporeforming rods and 18 clostridia. CLSI agar dilution MIC methodology with enriched *Brucella* blood agar and inocula of 1.times.10.sup.5 cfi/spot was used. Plates were incubated in an anaerobic glove box at 35° C. for 48 h.

Results. $MIC_{50}$/$MIC_{90}$ values (μg/ml) were as follows:

| Drug | *B. fragilis* gp (40) | Prev/Porphy (26) | Fusobacteria (28) | Gram + cocci (16) | Gram + rods (14) | Clostridia (18) | All (142) |
|---|---|---|---|---|---|---|---|
| Nitazoxanide | 2/4 | 4/8 | 1/4 | 0.5/2 | 16/>32 | 0.5/4 | 2/4 |
| Tizoxanide | 2/4 | 2/16 | 0.5/2 | 0.5/1 | 8/>32 | 0.25/2 | 2/4 |
| RM 4803 | >32/>32 | >32/>32 | >32/>32 | >32/>32 | >32/>32 | >32/>32 | >32/>32 |
| RM 4819 | >32/>32 | >32/>32 | >32/>32 | >32/>32 | >32/>32 | >32/>32 | >32/>32 |
| Amoxicillin-clavulanic acid | 1/4 | 0.06/0.5 | 0.5/4 | 0.125/0.5 | 0.25/1.0 | 0.125/1.0 | 0.5/2.0 |
| Clindamycin | 2/>32 | <0.015/<0.015 | 0.06/0.125 | 0.125/0.5 | 0.125/4 | 1/>32 | 0.125/8.0 |
| Metronidazole | 1/2 | 0.5/2 | 0.25/0.25 | 0.5/1.0 | >16/>16 | 0.25/2 | 1.0/2.0 |

Results showed that nitazoxanide, tizoxanide, potent against all anaerobic bacteria groups except for Gram-positive anaerobic rods including lactobacilli (which are in reality mostly microaerophils). By contrast, RM 4803 and RM 4819 were without significant activity.

EXAMPLE 3

Antiviral Activity

Compounds within Formula (IV) of the present invention exhibit potent antiviral activity, as shown in Table 5.

Activity of RM-4803, RM-4804 and RM-4806 against viruses in cell monolayer

| | Human Rhinovirus Type 39 OH-Hela 2% McCoys + Hepes Buffer | | Influenza A Virus MDCK 0% EMEM + Hepes + Trypsin | |
|---|---|---|---|---|
| Compound | Microscopic | Spectrophotometer | Microscopic | Spectrophotometer |
| $R_1$ = Br<br>$R_2$ = acetolyloxy<br>$R_3$ = methyl<br>(RM 4803) | 0.06 | 0.03 | 0.45 | 0.18 |
| $R_1$ = Cl<br>$R_2$ = acetolyloxy<br>$R_3$ = methyl<br>(RM 4804) | 0.57 | 0.32 | 0.93 | 0.57 |
| $R_1$ = Br<br>$R_2$ = acetolyloxy<br>$R_3$ = methoxy<br>(RM 4806) | 5.0 | 4.0 | 0.46 | 0.57 |
| Pirodavir | 0.007 | 0.004 | NA | NA |
| Oseltamivir | NA | NA | 0.13-0.17 | 0.08-0.36 |

$EC_{50}$ (.mu.g/mL) values for 2-(acetolyloxy)-3-methyl-N-(5-bromo-2-thiazolyl)benzamide (RM4803), 2-(acetolyloxy)-3-methyl-N-(5-chloro-2-thiazolyl)benzamide (RM4804), and 2-(acetolyloxy)-3-methoxy-N-(5-bromo-2-thiazolyl)benzamide (RM4806), on Human Rhinovirus Type 39 (HRV-39), and $H_3N_2$ influenza virus, type A, using a multiple cycle CPE inhibition assay on OH—I Hela and Madin Darby Canine Kidney (MDCK) cell monolayers, respectively, were measured by microscopic and spectrophotometric methods. Pirodavir and Oseltamivir were included as positive controls.

EXAMPLE 4

Selective Anti-Viral Activity

The above identified compounds according to Formula (IV) were tested by conventional means against *Trichomis vaginalis*, *Giardia Intestinalis*, and *Trypanosoma brucei*. 2-(acetolyloxy)-3-methyl-N-(5-bromo-2-thiazolyl)benzamide (RM4803), 2-(acetolyloxy)-3-methyl-N-(5-chloro-2-thiazolyl)benzamide (RM4804), and 2-(acetolyloxy)-3-methoxy-N-(5-bromo-2-thiazolyl)benzamide (RM4806) each failed to exhibit antiparasite activity against *Trichomonas vaginalis*, *Giardia intestinalis*, or *Trypanosoma brucei* at concentrations of at least 50 μg/mL.

Accordingly, it has been demonstrated that in accordance with the present invention, novel compounds can be provided which are generally characterized by selective antiviral activity.

As an additional benefit, it has been discovered that the above halogen-substituted benzamide compounds are effective against intracellular protozoa including *Cryptosporidium* spp., *Neospora* spp. and *Sarcocystis neurona* (RM-4820, RM-4821 and RM-4822).

With respect to the above description, it is to be realized that the optimum formulations and methods of the invention are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Certain references, patents and other printed publications have been referred to herein: the teachings and scope of each of said publications are hereby incorporated in their respect entireties by reference.

Now that the invention has been described:
What is claimed is:

1. A compound according to formula (III):

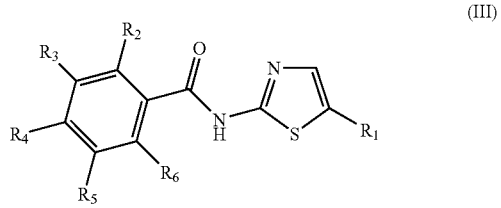

in which $R_1$ is a halogen atom, $R_2$-$R_6$ are independently hydrogen, halogen, nitro, hydroxyl, $C_1$-$C_4$ alkyl, —$C_1$-$C_4$ alkoxy, acyloxy, —C(O)$R_7$ where $R_7$ is —$C_1$-$C_4$ alkyl, or, aromatic including salts and hydrates of these compounds, wherein at least two of $R_2$-$R_6$ is other than hydrogen and at least one of $R_2$-$R_6$ is hydroxyl or acyloxy.

2. A compound as in claim 1, wherein at least one of $R_2$-$R_6$ is hydroxyl, and at least one of $R_2$-$R_6$ is halogen, nitro, $C_1$-$C_4$ alkyl, —$C_1$-$C_4$ alkoxy, acyloxy, —C(O)$R_7$ where $R_7$ is —$C_1$-$C_4$ alkyl, or aromatic, including salts and hydrates of these compounds.

3. A compound as in claim 1, wherein at least one of $R_2$-$R_6$ is acyloxy, and at least one of $R_2$-$R_6$ is halogen, nitro, $C_1$-$C_4$ alkyl, —$C_1$-$C_4$ alkoxy, hydroxy, —C(O)$R_7$ where $R_7$ is —$C_1$-$C_4$ alkyl, or aromatic, including salts and hydrates of these compounds.

4. A compound as in claim 1, wherein said acyloxy is acetoxy or propionoxy, and wherein said aromatic is phenyl or benzyl, which may be further substituted.

5. A compound as in claim 1, wherein $R_1$ is Br or Cl.

6. A compound as in claim 1, wherein two adjacent $R_2$-$R_6$ together form a benzyl ring.

7. A compound as in claim 1, selected from the group consisting of 2-(acetolyloxy)-3-methyl-N-(5-bromo-2-thiazolyl)benzamide (RM4803) and 2-(hydroxy)-3-methyl-N-(5-bromo-2-thiazolyl)benzamide (RM4819).

8. A compound as in claim 1, selected from the group consisting of 2-(acetolyloxy)-5-methyl-N-(5-chloro-2-thiazolyl)benzamide and 2-(hydroxy)-5-methyl-N-(5-chloro-2-thiazolyl)benzamide.

* * * * *